United States Patent [19]

Theodoridis

[11] Patent Number: 5,105,012

[45] Date of Patent: Apr. 14, 1992

[54] CATALYTIC REDUCTION OF DINITROBENZENES USING A NOBLE METAL CATALYST AND IRON OR IRON SALTS

[75] Inventor: George Theodoridis, Princeton, N.J.

[73] Assignee: FMC Corporation, Philadelphia, Pa.

[21] Appl. No.: 595,901

[22] Filed: Oct. 11, 1990

Related U.S. Application Data

[63] Continuation-in-part of Ser. No. 328,365, Mar. 24, 1989, abandoned.

[51] Int. Cl.$^5$ ............................................. C07C 209/36
[52] U.S. Cl. ........................................ 564/417; 71/88; 502/155; 502/185; 502/229; 502/326; 502/327; 548/251; 560/20; 562/73; 562/437; 564/418; 564/420; 564/422; 564/423
[58] Field of Search .............. 564/422, 423, 417, 418, 564/420, 440, 441; 560/20; 562/73, 437; 502/327

[56] References Cited

U.S. PATENT DOCUMENTS 4,212,824  7/1980  Seagraves ........................... 564/417

FOREIGN PATENT DOCUMENTS 127079  12/1984  European Pat. Off. .
58-04750  1/1983  Japan .
59-216855  12/1984  Japan .
61-36248  2/1986  Japan .

OTHER PUBLICATIONS

Ura et al., Chem. Abstracts 105:26137m (1986).
Chem. Abstracts 98:125604c (1983).
Seagraves, Chem. Abstracts 93:94965p (1980).
Cossaboon, Chem. Abstracts 92:146418p (1980).
Cossaboon, Chem. Abstracts 83:192794v (1975).
M. O. Terpko and R. F. Heck, "Palladium-Catalyzed Triethylammonium Formate Reductions, 3, Selective Reduction of Dinitroaromatic Compounds", *Journal of Organic Chemistry*, vol. 45, pp. 4492–4493 (1980).
M. Hudlicky and H. Bell, "2-Fluoro-3-Nitroaniline and 2-Fluoro-1,3-Phenylenediamine", *Journal of Fluorine Chemistry*, vol. 4, pp. 19–23 (1974).
Ignaczak et al., Chem. Abstracts 107:197648z (1987).
Mirza et al., Chem. Abstracts 107:8910v (1987).
Palleros et al., *Anales Asoc. Quim. Argentina*, vol. 70, No. 1, pp. 155–160 (1982).

Primary Examiner—Gennon H. Hollrah
Assistant Examiner—Scott C. Rand
Attorney, Agent, or Firm—Norman L. Craig; Robert M. Kennedy; Stanford M. Back

[57]  ABSTRACT

There is provided an improved process for the reduction of optionally substituted dinitrobenzenes to the corresponding nitroanilines with high yields which comprises contacting the dinitrobenzene with hydrogen in an acidic medium in the presence of a catalytic amount of a combination of a noble metal hydrogenation catalyst, and iron or an iron salt. Isomer specific reductions may be achieved with those compounds containing suitable directing substituents.

The 2-halo-5-nitroanilines which may be produced in this process may be converted via a multi-step synthesis to useful 1-aryl-4-substituted 1,4-dihydro-5H-tetrazol-5-one herbicides.

15 Claims, No Drawings

CATALYTIC REDUCTION OF DINITROBENZENES USING A NOBLE METAL CATALYST AND IRON OR IRON SALTS

This application is a continuation-in-part of application Ser. No. 328,365, filed on Mar. 24, 1989, now abandoned.

BACKGROUND OF THE INVENTION

This invention relates to a process for preparing useful intermediates in the synthesis of agricultural chemicals. More, particularly, it pertains to an improved process for the selective reduction of dinitrobenzenes to the corresponding nitroanilines which may then be utilized in the synthesis of triazolinone, tetrazolinone or related herbicides.

European Patent Application 127,079, Takemoto et al. (1984), discloses a process in which 2,4-dinitrofluorobenzene is selectively reduced using between 2.5 and 4 moles of iron in the presence of acid to produce one mole of 2-fluoro-5-nitroaniline. In one example in which acetic acid was employed and the reaction mixture was refluxed for ten minutes, 2-fluoro-5-nitroaniline was produced in 70% yield, by weight. The weight % ratio of the desired 2-fluoro-5-nitroaniline to the by-product 4-fluoro-3-nitroaniline was 93:7. The use of a noble metal catalyst is not taught by this patent application.

The reduction of nitrobenzene to aniline using iron with noble metal catalysts is also known from the prior art. See, for example, Chem. Abstracts 105:26137, Ura et al. (1986); Chem. Abstracts, 98:125,604, Mitsui Chemicals (1983); Chem. Abstracts 93:94965, Seegraves (1980); Chem. Abstracts 92:146418, Cossaboon (1980); and Chem. Abstracts 83:192794, Cossaboon (1975). None of these references, however, teaches the selective reduction of dinitrobenzenes or halogenated dinitrobenzenes.

In addition, the selective reduction of dinitro aromatic compounds using palladium-catalyzed hydrogenation with triethylammonium formate has been reported by Terpko et al., J. Org. Chem., 45, 4992 (1980). No 2,4-dinitrohalobenzenes were reported as being reduced. Those compounds which were reported as having been selectively reduced include 2,2'-dinitrobiphenyl, 1,3-dinitrobenzene, and various dinitrobenzenes substituted with methyl, hydroxy, methoxy, amino, methoxycarbonyl, and methylcarbonylamino groups.

SUMMARY OF THE INVENTION

In accordance with the present invention there is now provided an improved process for the reduction of optionally substituted dinitrobenzenes to form the corresponding nitroanilines in high yields, by contacting the dinitrobenzene with hydrogen, or a compound which may form a ready source of hydrogen, in an acidic medium in the presence of a mixture comprising a noble metal hydrogenation catalyst and a catalytic amount of iron or an iron salt.

Also when this improved reduction process is carried out using dinitrobenzenes in which a halogen or another electronegative atom or substituent is ortho to one of the nitro groups and para to the other, the ortho nitro group is selectively reduced. As a result of this isomer specific feature of the process, 2,4-dinitrofluorobenzene can be reduced to give a 90% yield of 2-fluoro-5-nitroaniline. Without the catalytic amount of iron or iron salt, selectivity and yields are substantially reduced.

In addition to high yields and selectivity, the present invention presents substantial benefits in requiring only catalytic amounts of iron to effect selective reduction. For example, the iron-acid reduction process which is disclosed in European Application 127,079 requires on the order of ten times as much iron to reduce the same quantity of a dinitrobenzene. The smaller amount of iron required in the present invention not only diminishes the size of the chemical reactor required, but also minimizes the amount of solid waste to be disposed of.

The products of this process may find utility as intermediates for dyestuffs and herbicides. For example, the 2-halo-5-nitroaniline products of this improved process may readily be converted to useful triazolinone or tetrazolinone herbicides. Thus, for example, starting with 2-fluoro-5-nitroaniline there may be prepared the tetrazolinone herbicide described in PCT Application US 86/02795, FMC Corp., (1987). In that application there is described a process where one may start with 2-fluoro-5-nitroaniline, and then make the corresponding isocyanate, which is converted to a tetrazolinone (as by treatment with trimethylsilyl azide). Reduction of the nitro group and substitution of an R group on N-4 of the tetrazolinone ring may take place in either order. Thereafter the amino group may be converted to an N-alkylsulfonylamino group, after which the compound may be halogenated (as with $SO_2Cl_2$ in dioxane) to place a halogen at the 4-position of the benzene ring, to obtain the corresponding 1-aryl-4-substituted-1,4-dihydro-5H-tetrazol-5-one compounds in accordance with the following reaction scheme:

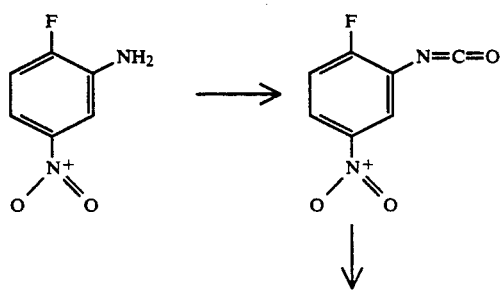

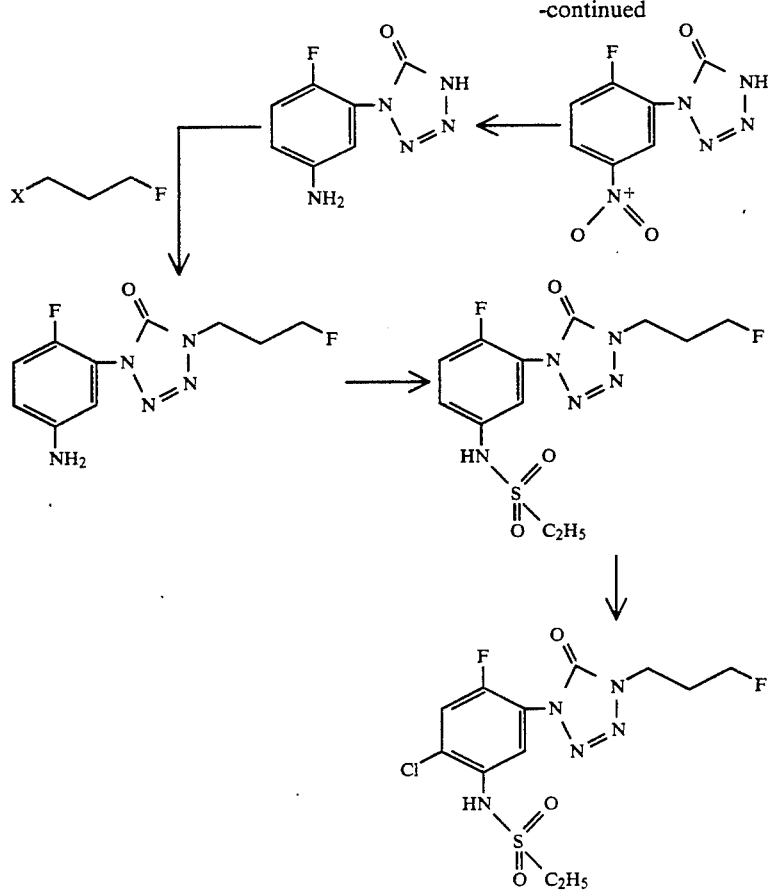

DETAILED DESCRIPTION OF THE INVENTION

The selective reduction of the dinitrobenzenes may generally be carried out in a known manner in a hydrogenation reactor, employing the catalysts and media of this invention, subject to controlling the amount of hydrogen used, as described below.

The noble metal catalysts employed herein include such known materials as palladium chloride, palladium on carbon, platinum oxide, rhodium on alumina, and the like. Of these palladium chloride is most preferred because of both its high selectivity and yield; palladium on carbon, which may provide a somewhat lower yield, is likewise desirable. As shown in the examples, platinum oxide, although it produces good yields, shows a reduced selectivity relative to palladium, while rhodium on alumina generally shows the converse, i.e. satisfactory selectivity although somewhat reduced yields. Significantly, it has been found that when no catalyst is present, as in Table 1, Example 45, no significant reaction occurs whatever.

The co-catalyst is preferably metallic iron or an iron salt, with metallic iron powder being favored. If an iron salt is used, a ferrous salt which is at least partially soluble in the reaction medium is desirable, preferably a salt of an organic acid. Ferrous acetate is preferred. Metallic zinc and copper, on the other hand, give low yields. As is shown in the tables, when the metallic iron or iron salt co-catalyst is omitted, both the nitroaniline yield and isomer selectivity are reduced.

The amount of noble metal catalyst employed should generally be in the range of from about 1.0 to 5.0 gms, more preferably 2.0 to 3.5 gms, per mole of the dinitrobenzene. The amount of iron co-catalyst should desirably be in the range of from about 2.8 gms (0.05 mole) to 44.8 gms (0.8 mole), preferably 5.6 gms (0.10 mole) to 19.6 gms (0.35 mole), per mole of the dinitrobenzene. An iron salt co-catalyst would be effective when used in concentrations which supply a similar amount of iron to the reaction system. Thus, the weight ratio of noble metal to iron is not critical and may be adjusted accordingly based on the nature of the noble metal, substrate, and the like.

In addition to the above catalyst combination, it is essential that the reaction be carried out in an acidic medium, as for example in the presence of a carboxylic acid such as acetic acid, propionic acid, trifluoroacetic acid, benzoic acid, or the like, preferably those acids having from about 1 to 4 carbon atoms. The amount of acid used may be as little as 10% or less by volume of the solvent mixture or as much as 100% of the solvent. Preferably, the solvent mixture will contain 20-80% by volume of the acid. Most preferably, the solvent mixture will contain 40-60% by volume of the acid.

Although not essential, the presence of an organic solvent has been found to enhance the yield. Such solvents as alcohols, e.g. ethanol; ethers, e.g. ethylene glycol dimethyl ether; or esters, e.g. ethyl acetate, or the like may thus be employed in combination with the acidic medium. The ratio of acid to solvent, if the latter is employed, is not critical and may be varied widely. For example, ratios of from about 9:1 to 1:4 (v:v) of ethanol to acetic acid are satisfactory for the purpose of providing high yields. Without an acid medium the reaction provides poor yields with low isomer selectivity.

The effect of the presence or absence of water on the yield of product is not clear. Comparison of examples such as Examples 30 and 33 might indicate that added water increases yield if platinum oxide is the catalyst. On the other hand there is a strong indication that the absence of water increases yield when palladium chloride is the catalyst (see Examples 13 and 14). Thus the use and amount, generally a small amount, of water must be judged on a case-by-case basis.

The substrate being reduced may be an unsubstituted dinitrobenzene, or any of a variety of mono or independently disubstituted dinitrobenzenes in which the substituents preferably do not sterically interfere with course of the reduction, and are substantially inert to the reaction conditions. Examples of such substituents include lower alkyl, halogen, fluoroalkyl, alkoxy, hydroxy, cyano, amino, mercapto, lower alkyl sulfonyl, sulfo ($-SO_3H$), lower alkyl thio, carboxy, lower alkyl oxycarbonyl, formyl, and lower alkyl carbonyl.

Isomeric selective reduction is also provided by this invention by the preferential reduction of nitro groups which are ortho to an electronegative atom or substituent attached to, or one atom removed from the aromatic ring. Examples of substituents which would effect isomeric selective reduction include halogen, hydroxy, alkoxy, fluoromethyl, cyano, mercapto, lower alkyl sulfonyl, sulfo-, lower alkyl thio, carboxy, lower alkyl oxycarbonyl, formyl, and lower alkyl carbonyl.

In this description whenever the terms appear, "halo" or "halogen" means fluorine, chlorine, or bromine. The term "alkyl" or "alkoxy" or the like implies a straight or branched hydrocarbon chain of 1-6 carbon atoms, preferably 1-4 carbon atoms. Lower alkyl implies 1-4 carbon atoms preferably 1-3 carbon atoms. The term "halo" modifying "alkyl", "cycloalkyl", or "alkoxy" or the like means one or more hydrogen atoms has been replaced by halogen.

In the above process the nitro groups are preferably meta to one another. To achieve isomeric selective reduction, the electronegative substituent or group is preferably ortho to the nitro group which is to be reduced, and para to the other nitro group. The substrate of choice is 2,4-dinitrofluorobenzene.

In addition to hydrogen itself there may also be employed hydrogen precursors, i.e. materials which under the conditions of the reaction give off hydrogen in necessary amounts. Among these is ammonium formate which may be used in place of hydrogen in combination with the hydrogenation catalysts of this invention, preferably palladium on carbon and powdered iron.

In carrying out this process it is important to have adequate hydrogen continuously available to avoid any interruption of the reaction. The yields are significantly improved by stopping the reaction when about three equivalents of hydrogen per nitro group to be reduced have been used. Failure to stop the reaction at this point will generally result in increased reduction of the second nitro group and a lower-than-optimum yield.

The temperatures and pressures employed in this selective reduction process are not critical and are those generally known in the art for reducing nitro to amino groups. For example, temperatures from about 10° to 50° C., preferably 20° to 40° C. may be used, together with commensurate hydrogen pressure, e.g. 200 psi, depending upon the amount of starting materials, and the like. Thus, these conditions, together with time and quantities, may be varied routinely as needed.

This process will now be illustrated by, but not limited to, the following examples as set forth in Tables 1 to 4. Certain of these examples are first set forth in detail; the remaining examples have been carried out in the same general manner except for variations in catalysts, reaction conditions and the like as set forth in each table. In each of the tables, the % yield is calculated from the weight of product, assuming it to be comprised of the corresponding nitroanilines with negligible amounts of other products and starting material, and is based on the number of moles of dinitrobenzene charged to the reactor. Since two isomers, e.g. 2-halo-5-nitroaniline and 4-halo-3-nitroaniline, can be produced by this reduction, the terms "purity" and "selectivity" refer to the percentage of 2-substituted-5-nitroaniline in this mixture. To obtain a % yield of 2-halo-5-nitroaniline, it is only required that the previously calculated yield be multiplied by the percent purity. In those cases in which reduction of either nitro group would give the same product, or in which the substituent is not directing (e.g. methyl in 2,4-dinitrotoluene), the % yield is based on the total amount of nitroaniline produced (Table 3).

The absence of a recorded reaction time in the tables for certain reactions merely reflects the lack of criticality of this variable. Rather, the factor which determined the length of the reaction time was the amount of hydrogen required in the experiment. In the optimum reactions this was 3 moles of hydrogen per mole of a dinitrobenzene. Reaction times under these conditions using, for example, 0.1 moles of 2,4-dinitrofluorobenzene were preferably between 30 minutes and 100 minutes.

The method of measuring the amount of hydrogen introduced into the reaction system depends on the system itself. In all reactions reported using gaseous hydrogen, a reactor of known volume at a known temperature was pressured with hydrogen initially and was repressured as the hydrogen was consumed until the correct amount of hydrogen had been introduced into the reactor.

EXAMPLE 13

Hydrogenation of 2,4-Dinitrofluorobenzene Using Palladium Chloride and Powdered Iron in the Absence of Water Powdered iron (1.5 g, 0.027 mole) and palladium chloride (0.40 g, 0.00022 mole) were ground together in a mortar and pestle. This mixture was placed in a 500 ml Parr hydrogenation reactor together with 17.23 g (0.0926 mole) of 2,4-dinitrofluorobenzene, 100 ml of ethanol, and 100 ml of glacial acetic acid. The reaction was allowed to proceed for 30 minutes during which time 347 psi of hydrogen was absorbed by the reaction mixture. The temperature of the dark red reaction mixture was 50° C. when it was filtered. The filtrate was diluted with water, causing a light red solid to precipitate. This solid weighed 13.70 g; m.p. 94°–95° C. The nmr spectrum confirmed that it was 2-fluoro-5-nitroaniline (95% purity).

EXAMPLE 23

Hydrogenation of 2,4-Dinitrofluorobenzene Using 5% Palladium on Carbon and Powdered Iron To a 500 ml Parr hydrogenation reactor were charged 8.1 g (0.0438 mole) of 2,4-dinitrofluorobenzene, 0.5 g of 5% palladium on carbon catalyst, 1.0 g (0.018 mole) of powdered iron, 150 ml of ethanol, 50 ml of glacial acetic acid, and 5 ml of water. The reaction was stopped after 152 psi of hydrogen had been absorbed. The reaction mixture was filtered, and the filtrate was evaporated under reduced pressure leaving a red solid. This solid was passed through a pad of silica gel, eluting with methylene chloride. The solvent was evaporated from the eluate, producing 5.85 g of crude 2-fluoro-5-nitroaniline, m.p. 94°–96° C. Analysis of the nmr spectrum of this material showed it to be >90% pure 2-fluoro-5-nitroaniline.

EXAMPLE 26

Reduction of 2,4-Dinitrofluorobenzene Using 10% Palladium on Carbon and Powdered Iron in the Presence of Ammonium Formate A solvent mixture was prepared by mixing 45 ml of ethanol, 45 ml of glacial acetic acid, and 10 ml of water. A portion of this solvent mixture (30 ml) was placed in a flask together with 0.2 g of 10% palladium on carbon catalyst, and 0.2 g of powdered iron. This mixture was stirred for 20 minutes after which 2.79 g (0.0150 mole) of 2,4-dinitrofluorobenzene in another portion of the solvent mixture was added. This mixture was cooled and maintained at 10°–15° C. while a solution of 2.85 g (0.0452 mole) of ammonium formate was added with the remainder of the solvent mixture. The reaction was stirred for two hours during which the temperature was maintained at 15°–18° C. The reaction mixture was stirred for five hours more and was filtered. The filtrate was evaporated under reduced pressure, leaving a residue which was then dissolved in ethyl acetate. This solution was washed in succession with water and a saturated aqueous solution of sodium bicarbonate. After being dried over anhydrous magnesium sulfate, the solution was treated with silica gel and then with charcoal. The solution was filtered, and the yellow filtrate was evaporated, leaving a brown solid residue weighing 1.94 g. The nmr spectrum of this residue was consistent with the product being 2-fluoro-5-nitroaniline. The purity of this product as determined by gas chromatography was 88%.

EXAMPLE 30

Hydrogenation of 2,4-Dinitrofluorobenzene Using Platinum Oxide and Powdered Iron To a mixture of 40 ml of glacial acetic acid, 5 ml of water, and 8.32 g (0.0447 mole) of 2,4-dinitrofluorobenzene were added 0.10 g (0.00044 mole) of platinum oxide and 0.50 g (0.0090 mole) of powdered iron. Subsequently, 160 ml of ethanol was added to this mixture, and the entire reaction mixture was placed in a 500 ml Parr hydrogenation reactor. The reaction was stopped after 144 psi of hydrogen had been absorbed, and the reaction mixture was then filtered. The filtrate was evaporated under reduced pressure, and the residue was passed through a pad of silica gel, eluting with methylene chloride. The solvent was evaporated from the eluate under reduced pressure, producing 6.23 g of crude 2-fluoro-5-nitroaniline, m.p. 90°–92° C. Analysis of the nmr spectrum of this material showed it to be at least 85% pure 2-fluoro-5-nitroaniline.

EXAMPLE 40

Hydrogenation of 2,4-Dinitrofluorobenzene Using 5% Rhodium on Alumina and Powdered Iron In a 500 ml Parr hydrogenation reactor were placed 8.50 g (0.0457 mole) of 2,4-dinitrofluorobenzene, 1.0 g (0.018 mole) of powdered iron, 0.15 g of 5% rhodium on alumina, 100 ml of ethanol, 100 ml of acetic acid, and 5 ml of water. The reaction was stopped after 140 psi of hydrogen had been absorbed, and the reaction mixture was then filtered. The filtrate was concentrated under reduced pressure, and water was added to the residue. Filtration yielded 5.62 g of crude 2-fluoro-5-nitroaniline. Analysis of the nmr spectrum of the product showed it to be >90% pure 2-fluoro-5-nitroaniline.

EXAMPLE 69

Hydrogenation of 2,4-Dinitrofluorobenzene Using Palladium Chloride and Ferrous Acetate Palladium chloride (0.35 gram, 0.002 mole) and ferrous acetate (4.34 grams, 0.025 mole) were ground together in a mortar and pestle. This mixture was placed in a 500 mL Parr hydrogenation reactor together with 18.61 grams (0.10 mole) of 2,4-dinitrofluorobenzene, 100 mL of glacial acetic acid, and 100 mL of anhydrous ethanol. The reaction was allowed to proceed for 30 minutes during which time 370 psi of hydrogen was absorbed by the reaction mixture. The reaction mixture was then poured into 400 mL of water, and this mixture was extracted twice with 200 mL of diethyl ether. The extracts were dried with anhydrous magnesium sulfate, and the diethyl ether was evaporated under reduced pressure. The liquid residue was run through a plug of silica gel, eluting with methylene chloride. The recovered material weighed 13.73 grams, and an NMR spectrum of it revealed that it was 90% 2-fluoro-5-nitroaniline and 10% 4-fluoro-3-nitroaniline. This product was further purified by column chromatography on silica gel, eluting with methylene chloride:heptane (80:20). The purified product, 2-fluoro-5-nitroaniline, weighed 12.29 grams; m.p. 99°–100° C. This is a 78.7% yield of purified product.

EXAMPLE 25

Hydrogenation of 2,4-Dinitrofluorobenzene Using 5% Palladium on Carbon as Catalyst In a 500 mL Parr hydrogenation apparatus were placed 18.61 grams (0.10 mole) Of 2,4-dinitrofluorobenzene, 0.5 gram of 5% palladium on carbon catalyst, 100 mL glacial acetic acid, 100 mL of anhydrous ethanol. The apparatus was equipped with a thermocouple and a cooling jacket. The temperature of the reaction mixture was maintained at 20°–25° C. during the reaction which consumed 370 psi of hydrogen and required 2.5 hours. The reaction mixture was then poured into 400 mL of water. This mixture was extracted twice with 200 mL, and the extracts were dried with anhydrous magnesium sulfate. The solvent was evaporated under reduced pressure, leaving a residue which was passed through a pad of silica gel, eluting with methylene chloride. This solvent was evaporated under reduced pressure, and the residue was purified by column chromatography, eluting with methylene chloride:heptane (80:20). After evaporation of the solvent under reduced pressure, the 2-fluoro-5-nitroaniline that was isolated weighed 2.75 grams, a 17.6% yield.

EXAMPLE 43

Hydrogenation of 2,4-Dinitrofluorobenzene Using 5% Rhodium on Alumina as Catalyst Using the method described in Example 25, 18.61 grams (0.10 mole) of 2,4-dinitrofluorobenzene was hydrogenated in the presence of 0.50 gram of rhodium on alumina hydrogenation catalyst in 100 mL each of glacial acetic acid and anhydrous ethanol. During the reaction which required two hours, a total of 370 psi of hydrogen was consumed. The 2-fluoro-5-nitroaniline recovered by column chromatography weighed 2.79 grams, a 17.6% yield. Also, 0.85 gram of 4-fluoro-3-nitroaniline was recovered as a second fraction.

EXAMPLE 8

Hydrogenation of 2,4-Dinitrofluorobenzene Using Palladium Chloride as Catalyst

Using the method described in Example 25, 8.16 grams (0.044 mole) of 2,4-dinitrofluorobenzene was hydrogenated in the presence cf 0.20 gram (0.0011 mole) of palladium (II) chloride in 100 mL each of glacial acetic acid and anhydrous ethanol. The crude product that was isolated weighed 1.67 grams and was determined to be 68% 2-fluoro-5-nitroaniline by NMR, a yield of 16.5%. The sample was purified by column chromatography, yielding 1.1 grams of 2-fluoro-5-nitroaniline, an isolated yield of 16.1%. A 0.18 gram fraction of 4-fluoro-3-nitroaniline was also recovered.

TABLE 1

HYDROGENATIONS OF 2,4-DINITROFLUOROBENZENE USING NOBLE METAL CATALYSTS WITH AND WITHOUT POWDERED IRON AS CO-CATALYST

| Example | Reactant[a] (Moles) | Catalyst Type | Catalyst (Grams) | Co-catalyst[b] (Grams) | Ethanol (ml) | Acetic Acid (ml) | Water (ml) | Product (Grams) | Yield (%) | Selectivity[c] (%) | Time (min.) |
|---|---|---|---|---|---|---|---|---|---|---|---|
| 1 | 0.093 | PdCl$_2$ | 0.20 | 0.5 | 100 | 100 | — | 12.98 | 89.4 | 89 | N/A |
| 2 | 0.044 | PdCl$_2$ | 0.10 | 0.5 | 100 | 100 | — | 4.50 | 65.5 | 84 | 45 |
| 3 | 0.044 | PdCl$_2$ | 0.10 | 0.5 | 100 | 100 | — | 5.50 | 80.1 | 89 | N/A |
| 4 | 0.044 | PdCl$_2$ | 0.20 | 0.5 | 100 | 100 | — | 4.8 | 69.9 | 83 | 20 |
| 5 | 0.044 | PdCl$_2$ | 0.20 | 0.5 | 100 | 100 | — | 5.5 | 80.1 | 90 | 25 |
| 6 | 0.044 | PdCl$_2$ | 0.20 | 0.5 | 100 | 100 | — | 6.1 | 88.1 | 91 | N/A |
| 7 | 0.044 | PdCl$_2$ | 0.20 | 0.5 | 100 | 100 | — | 4.5 | 65.5 | 93 | N/A |
| 8 | 0.044 | PdCl$_2$ | 0.20 | 0 | 100 | 100 | — | 1.67 | 16.5 | 68 | 120 |
| 9 | 0.044 | PdCl$_2$ | 0.20 | 1.0 | 100 | 100 | 5 | 4.5 | 65.5 | N/A[k] | 225 |
| 10 | 0.100 | PdCl$_2$ | 0.35 | 1.4 | 100 | 100 | — | 14.75 | 94.4 | 93 | 45 |
| 11 | 0.100 | PdCl$_2$ | 0.35 | 1.4 | 100 | 100 | — | 14.25 | 91.3 | 96 | 75 |
| 12 | 0.100 | PdCl$_2$ | 0.35 | 1.4· | 100 | 100 | — | 14.75 | 94.4 | 93 | 75 |
| 13 | 0.093 | PdCl$_2$ | 0.40 | 1.5 | 100 | 100 | — | 13.70 | 94.8 | 95 | 30 |
| 14 | 0.044 | PdCl$_2$ | 0.20 | 1.0 | 100 | 100 | 5 | 6.1 | 89.2 | N/A | N/A |
| 15 | 0.044 | PdCl$_2$ | 0.20 | 2.0 | 100 | 100 | 5 | 5.4 | 79.0 | N/A | N/A |
| 16 | 0.051 | PdCl$_2$ | 0.20 | 2.0 | 100 | 100 | 5 | 5.62 | 70.6 | N/A | N/A |
| 17 | 0.044 | PdCl$_2$ | 0.20 | 1.0 | 180 | 20[d] | — | 3.69 | 53.7 | 53 | 90 |
| 18 | 0.100 | PdCl$_2$ | 0.35 | 1.4 | 100[e] | 100 | — | 12.50 | 80.1 | 88 | 80 |
| 19 | 0.043 | PdCl$_2$ | 0.4 | 1.0[f] | 100 | 100 | — | 1.0 | 14.9 | N/A | N/A |
| 20 | 0.043 | PdCl$_2$ | 0.4 | 1.0[g] | 100 | 100 | | No Reaction | | | N/A |
| 21 | 0.093 | 5% Pd/C | 0.5 | 0.50 | 100 | 100 | — | 12.65 | 87.1 | 90 | N/A |
| 22 | 0.100 | 5% Pd/C | 0.50 | 1.4 | 100 | 100 | — | 14.15 | 90.6 | 88 | 36 |
| 23 | 0.044 | 5% Pd/C | 0.5 | 1.0 | 150 | 50 | 5 | 5.85 | 85.6 | >90 | N/A |
| 24 | 0.044 | 5% Pd/C | 0.5 | 2.0 | 100 | 150 | 5 | 5.83 | 85.6 | >90 | N/A |
| 25 | 0.100 | 5% Pd/C | 0.5 | 0 | 100 | 100 | — | 2.75 | 17.6 | N/A | 150 |
| 26 | 0.015[h] | 10% Pd/C | 0.2 | 0.2 | 45 | 45 | 10 | 1.94 | 82.8 | 88 | 420 |
| 27 | 0.005[i] | 10% Pd/C | 0.2 | 0.14 | 27 | — | 3 | 0.15 | 19.2 | N/A | N/A |
| 28 | 0.093 | PtO$_2$ | 0.20 | 0.50 | 100 | 100 | — | 12.73 | 87.7 | 85 | N/A |
| 29 | 0.046 | PtO$_2$ | 0.10 | 0.5 | 200 | — | — | No Reaction | | | N/A |
| 30 | 0.045 | PtO$_2$ | 0.10 | 0.50 | 160 | 40 | 5 | 6.23 | 89.2 | 85 | N/A |
| 31 | 0.045 | PtO$_2$ | 0.10 | 0.50 | 80 | 120 | 10 | 5.60 | 80.6 | N/A | N/A |
| 32 | 0.045 | PtO$_2$ | 0.10 | 0.50 | — | 200 | 10 | 4.9 | 70.5 | N/A | N/A |
| 33 | 0.044 | PtO$_2$ | 0.10 | 0.50 | 150 | 50 | — | 5.96 | 86.2 | N/A | N/A |
| 34 | 0.044 | PtO$_2$ | 0.15 | 1.00 | 100 | 100 | 5 | 5.60 | 81.5 | N/A | N/A |
| 35 | 0.100 | PtO$_2$ | 0.35 | 1.40 | 200 | — | — | 3.15 | 20.2 | N/A | N/A |
| 36 | 0.100 | PtO$_2$ | 0.45 | 1.40 | 100 | 100 | — | 14.20 | 91.0 | 88 | 35 |
| 37 | 0.043 | PtO$_2$ | 0.4 | 0 | 100 | 100 | — | 2.1 | 31.3 | N/A | N/A |
| 38 | 0.043 | PtO$_2$ | 0.4 | 0 | 100 | 100 | — | 1.55 | 23.1 | N/A | N/A |
| 39 | 0.043 | PtO$_2$ | 0.4 | 1.0[j] | 100 | 100 | — | 2.47 | 36.8 | N/A | N/A |
| 40 | 0.046 | 5% Rh/Al$_2$O$_3$ | 0.15 | 1.0 | 100 | 100 | 5 | 5.62 | 78.8 | >90 | N/A |
| 41 | 0.043 | 5% Rh/Al$_2$O$_3$ | 0.15 | 1.0 | 160 | 80 | 2 | 5.15 | 76.7 | >90 | N/A |
| 42 | 0.100 | 5% Rh/Al$_2$O$_3$ | 0.50 | 1.4 | 100 | 100 | — | 14.1 | 90.3 | 82 | 65 |
| 43 | 0.100 | 5% Rh/Al$_2$O$_3$ | 0.50 | 0 | 100 | 100 | — | 3.23 | 20.7 | >85% | 120 |
| 44 | 0.043 | 5% Rh/Al$_2$O$_3$ | N/A | 0 | — | 200 | — | No Reaction | | | 60 |

TABLE 1-continued

HYDROGENATIONS OF 2,4-DINITROFLUOROBENZENE USING
NOBLE METAL CATALYSTS WITH AND WITHOUT POWDERED IRON AS CO-CATALYST

| | Reactant[a] | Catalyst | | Co-catalyst[b] | Solvents | | | Product | Yield | Selectivity[c] | Time |
|---|---|---|---|---|---|---|---|---|---|---|---|
| | | | | | Ethanol | Acetic Acid | Water | | | | |
| Example | (Moles) | Type | (Grams) | (Grams) | (ml) | (ml) | (ml) | (Grams) | (%) | (%) | (min.) |
| 45 | 0.044 | None | | 1 | 100 | 100 | 10 | No Reaction | | | N/A |

[a]2,4-Dinitrofluorobenzene
[b]Co-catalyst is powdered iron unless otherwise specified
[c]Percentage of 2-fluoro-5-nitroaniline in product
[d]37% Hydrochloric acid in place of acetic acid
[e]1,2-Dimethoxyethane in place of ethanol
[f]Powdered zinc in place of powdered iron
[g]Copper wire in place of powdered iron
[h]Reaction mixture contained 2.85 g (0.0452 mole) of ammonium formate
[i]Reaction mixture contained 0.95 g (0.015 mole) of ammonium formate
[j]Powdered copper in place of powdered iron
[k]Not available

TABLE 2

HYDROGENATIONS OF 2,4-DINITROPHENOL AND 2,4-DINITROCHLOROBENZENES
USING NOBLE METAL CATALYSTS WITH AND WITHOUT POWDERED IRON AS CO-CATALYST

| | Reactant | Catalyst | | Iron Co-catalyst | Solvents | | Water | Product | Yield | Time |
|---|---|---|---|---|---|---|---|---|---|---|
| | | | | | Ethanol | Acetic Acid | | | | |
| Example | (Moles) | Type | (Grams) | (Grams) | (ml) | (ml) | (ml) | (Grams) | (%) | (min.) |
| 46 | 0.100[a] | PdCl$_2$ | 0.35 | 1.4 | 100 | 100 | — | 11.98 | 77.7 | 60 |
| 47 | 0.100[a] | PdCl$_2$ | 0.35 | 1.4 | 100 | 100 | — | 12.17 | 79.0 | ~170 |
| 48 | 0.025[a] | PdCl$_2$ | 0.35 | 0 | 100 | 100 | — | 1.60 | 41.5 | 15 |
| 49 | 0.043[b] | PdCl$_2$ | 0.40 | 1.0 | 100 | 100 | — | 6.0 | 80.9 | N/A |
| 50 | 0.100[b] | PdCl$_2$ | 0.35 | 1.4 | 100 | 100 | — | 10.49 | 60.8 | N/A |
| 51 | 0.100[b] | PdCl$_2$ | 0.35 | 0 | 100 | 100 | — | 1.87 | 10.8 | 105 |
| 52 | 0.049[b] | 5% Pd/C | 0.12 | 1.2 | 100 | 100 | 5 | 7.50[d] | 88.0 | N/A |
| 53 | 0.100[c] | PdCl$_2$ | 0.35 | 1.4 | 100 | 100 | — | 18.66 | 90.1 | 50 |
| 54 | 0.100[c] | PdCl$_2$ | 0.35 | 1.4 | 100 | 100 | — | 18.20 | 87.9 | 75 |
| 55 | 0.100[c] | PdCl$_2$ | 0.35 | 0 | 100 | 100 | — | 3.21 | 15.5 | 222 |

[a]2,4-Dinitrophenol
[b]2,4-Dinitrochlorobenzene
[c]1,5-Dichloro-2,4-dinitrobenzene
[d]about 75% 2-chloro-5-nitroaniline

TABLE 3

HYDROGENATIONS OF DINITROBENZENES AND
2,4-DINITROTOLUENE USING NOBLE METAL CATALYSTS
WITH AND WITHOUT POWDERED IRON AS CO-CATALYST

| | Reactant | Catalyst | | Iron Co-catalyst | Solvents | | Product | Yield | Time |
|---|---|---|---|---|---|---|---|---|---|
| | | | | | Ethanol | Acetic Acid | | | |
| Example | (Moles) | Type | (Grams) | (Grams) | (ml) | (ml) | (Grams) | (%) | (min.) |
| 56 | 0.100[a] | PdCl$_2$ | 0.35 | 1.4 | 100 | 100 | 10.98 | 79.5 | N/A |
| 57 | 0.100[a] | PdCl$_2$ | 0.35 | 1.4 | 100 | 100 | 10.0 | 72.4 | N/A |
| 58 | 0.043[a] | PdCl$_2$ | 0.20 | 1.0 | 50 | 50 | 4.2 | 70.7 | N/A |
| 59 | 0.100[a] | PdCl$_2$ | 0.35 | 0 | 100 | 100 | 2.89 | 20.9 | N/A |
| 60 | 0.100[a] | PdCl$_2$ | 0.35 | 0 | 100 | 100 | 1.90 | 13.8 | 50 |
| 61 | 0.100[b] | PdCl$_2$ | 0.35 | 1.4 | 100 | 100 | 11.05 | 80.0 | N/A |
| 62 | 0.100[b] | PdCl$_2$ | 0.35 | 0 | 100 | 100 | 1.86 | 13.5 | 315 |
| 63 | 0.043[a] | PtO$_2$ | 0.20 | 1.0 | 50 | 50 | 4.7 | 79.1 | N/A |
| 64 | 0.086[a] | PtO$_2$ | 0.40 | 1.0 | 100 | 100 | 10.0 | 84.4 | N/A |
| 65 | 0.043[c] | PdCl$_2$ | 0.40 | 1.0 | 100 | 100 | 4.7[d] | 71.8 | N/A |
| 66 | 0.043[c] | PdCl$_2$ | 0.40 | 1.0 | 100 | 100 | 3.0[e] | 45.9 | N/A |
| 67 | 0.100[c] | PdCl$_2$ | 0.35 | 1.4 | 100 | 100 | 7.89[f] | 51.8 | N/A |
| 68 | 0.100[c] | PdCl$_2$ | 0.35 | 0 | 100 | 100 | 4.31[g] | 28.3 | 93 |

[a]1,3-Dinitrobenzene
[b]1,4-Dinitrobenzene
[c]2,4-Dinitrotoluene
[d]31.8% 2-Methyl-5-nitroaniline
[e]47% 2-Methyl-5-nitroaniline
[f]greater than 54.9% 2-methyl-5-nitroaniline
[g]53.4% 2-Methyl-5-nitroaniline

TABLE 4

HYDROGENATIONS OF 2,4-DINITROFLUOROBENZENES USING PALLADIUM CHLORIDE AND FERROUS ACETATE AS CO-CATALYST

| Example | Reactant[a] (Moles) | PdCl$_2$ (Grams) | Fe(OAc)$_2$ (Grams) | Solvents | | Product (Grams) | Yield (%) | Selectivity[b] (%) | Time (min.) |
|---|---|---|---|---|---|---|---|---|---|
| | | | | Ethanol (ml) | Acetic Acid (ml) | | | | |
| 69 | 0.100 | 0.35 | 4.34 | 100 | 100 | 13.73 | 87.9 | 90 | 30 |
| 70 | 0.100 | 0.35 | 1.74 | 100 | 100 | 10.95 | 70.1 | 90 | 43 |

[a]2,4-Dinitrofluorobenzene
[b]Percentage of 2-fluoro-5-nitroaniline in product

I claim:

1. A process for the selective reduction of dinitrobenzenes, or mono- or independently di-substituted dinitrobenzenes to form the corresponding nitroanilines which comprises contacting a dinitrobenzene or mono- or di-substituted dinitrobenzene with hydrogen in an acidic medium in the presence of a noble metal catalyst, and a catalytic amount of a co-catalyst of iron or an iron salt.

2. A process of claim 1 in which the substituted dinitrobenzene is substituted with lower alkyl, halogen, fluoroalkyl, alkoxy, hydroxy, cyano, amino, mercapto, lower alkyl sulfonyl, sulfo, lower alkyl thio, carboxy, lower alkyl, oxycarbonyl, formyl, or lower alkyl carbonyl.

3. A process of claim 2 in which between 0.05 and 0.8 moles of co-catalyst is used for each mole of dinitrobenzene.

4. A process of claim 3 in which the co-catalyst is iron or ferrous acetate.

5. A process of claim 4 in which the process is carried out in the presence of an organic acid.

6. A process of claim 5 in which the noble metal catalyst is palladium on carbon, palladium chloride, platinum oxide, or rhodium on alumina.

7. A process of claim 6 in which between 0.1 and 0.35 moles of co-catalyst is used for each mole of dinitrobenzene.

8. A process of claim 7 in which the substituted dinitrobenzene is substituted with halogen, hydroxy, or lower alkyl.

9. A process of claim 5 in which the organic acid is acetic acid.

10. A process of claim 5 in which the process is optionally carried out in the presence of an organic solvent.

11. A process of claim 6 in which the co-catalyst is powdered iron.

12. A process for the selective reduction of 2,4-dinitrofluorobenzene to form the corresponding 2-fluoro-5-nitroaniline which comprises contacting the 2,4-dinitrofluorobenzene with hydrogen in a medium containing acetic acid in the presence of a palladium chloride catalyst and powdered iron.

13. A process of claim 12 in which between 0.05 and 0.8 moles of powdered iron is used for each mole of the 2,4-dinitrofluorobenzene.

14. A process of claim 13 in which no greater than about three equivalents of hydrogen are employed for each mole of 2,4-dinitrofluorobenzene.

15. A process of claim 14 in which the hydrogen is provided continuously.

* * * * *